(12) United States Patent
Mallet et al.

(10) Patent No.: US 12,100,807 B2
(45) Date of Patent: Sep. 24, 2024

(54) ADDITIVES FOR ELECTROLYTES IN Li-IONS BATTERIES

(71) Applicants: HYDRO-QUÉBEC, Montréal (CA); MURATA MANUFACTURING CO., LTD., Nagaokakyo (JP)

(72) Inventors: Charlotte Mallet, Montréal (CA); Sylviane Rochon, Saint-Adèlphe (CA); Karim Zaghib, Longueuil (CA)

(73) Assignees: HYDRO-QUÉBEC, Montreal (CA); MURATA MANUFACTURING CO., LTD., Nagaokakyo (JP)

( * ) Notice: Subject to any disclaimer, the term of this patent is extended or adjusted under 35 U.S.C. 154(b) by 658 days.

(21) Appl. No.: 17/281,120

(22) PCT Filed: Oct. 3, 2019

(86) PCT No.: PCT/CA2019/051415
§ 371 (c)(1),
(2) Date: Mar. 29, 2021

(87) PCT Pub. No.: WO2020/069619
PCT Pub. Date: Apr. 9, 2020

(65) Prior Publication Data
US 2021/0376381 A1 Dec. 2, 2021

Related U.S. Application Data

(60) Provisional application No. 62/741,275, filed on Oct. 4, 2018.

(51) Int. Cl.
*H01M 10/0567* (2010.01)
*C07C 255/50* (2006.01)
(Continued)

(52) U.S. Cl.
CPC ....... *H01M 10/0567* (2013.01); *C07C 255/50* (2013.01); *C07C 255/51* (2013.01);
(Continued)

(58) Field of Classification Search
None
See application file for complete search history.

(56) References Cited

U.S. PATENT DOCUMENTS

2004/0013946 A1 1/2004 Abe et al.
2009/0197167 A1 8/2009 Olschimke
(Continued)

FOREIGN PATENT DOCUMENTS

CA 2913195 A1 12/2014
CA 3005799 A1 6/2017
(Continued)

OTHER PUBLICATIONS

Extended European Search Report dated Jul. 15, 2022, issued by the European Patent Office in corresponding European Application No. 19868859.0-1108, (15 pages).
(Continued)

*Primary Examiner* — Eli S Mekhlin
(74) *Attorney, Agent, or Firm* — Womble Bond Dickinson (US) LLP

(57) ABSTRACT

Method of improving the performance and safety of a Li-ion battery. The method includes using a nitrile-based small organic compound of general formula I, V or IX outlined in the application in association with the electrolyte of the battery. An electrolyte including a nitrile-based small organic compound. A battery including the electrolyte.

11 Claims, 11 Drawing Sheets

(51) Int. Cl.

| | | |
|---|---|---|
| *C07C 255/51* | (2006.01) | |
| *C07C 255/55* | (2006.01) | |
| *C07D 213/57* | (2006.01) | |
| *H01M 10/0525* | (2010.01) | |
| *H01M 10/42* | (2006.01) | |

(52) U.S. Cl.
CPC .......... *C07C 255/55* (2013.01); *C07D 213/57* (2013.01); *H01M 10/0525* (2013.01); *H01M 10/4235* (2013.01)

(56) References Cited

U.S. PATENT DOCUMENTS

| | | | |
|---|---|---|---|
| 2011/0129738 A1 | 6/2011 | Kawashima | |
| 2012/0208080 A1 | 8/2012 | Park et al. | |
| 2012/0270092 A1 | 10/2012 | Honbou et al. | |
| 2014/0356735 A1 | 12/2014 | Pena Hueso et al. | |
| 2018/0034106 A1 | 2/2018 | Schmidt | |
| 2021/0111432 A1* | 4/2021 | Saidi | H01M 10/0569 |

FOREIGN PATENT DOCUMENTS

| | | |
|---|---|---|
| CN | 1487621 A | 4/2004 |
| CN | 101283466 A | 10/2008 |
| CN | 102088111 A | 6/2011 |
| CN | 102646846 A | 8/2012 |
| CN | 102751532 A | 10/2012 |
| CN | 104837850 A | 8/2015 |
| CN | 105 591 156 A | 5/2016 |
| CN | 104 051 786 B | 6/2016 |
| CN | 107 403 959 A | 11/2017 |
| CN | 107408727 A | 11/2017 |
| CN | 107 785 610 A | 3/2018 |
| CN | 108 054 430 A | 5/2018 |
| CN | 108428939 A | 8/2018 |
| DE | 102005048802 A1 | 4/2007 |
| EP | 0 322 738 A2 | 7/1989 |
| EP | 2 490 292 A1 | 8/2012 |
| FR | 1517178 A | 3/1968 |
| JP | H03236168 A | 10/1991 |
| JP | 2002023394 A | 1/2002 |
| JP | 2002302649 | 10/2002 |
| JP | 2004165050 | 6/2004 |
| JP | 2014096213 A | 5/2014 |
| JP | 2018508112 | 3/2018 |
| WO | 2016146925 A1 | 9/2016 |
| WO | 2017113820 | 7/2017 |
| WO | 2018056776 | 3/2018 |

OTHER PUBLICATIONS

Turpaev, et al:"Benzylidenemalononitrile compounds as activators of cell resistance to oxidative stress and modulators of multiple signaling pathways. A structure-activity relationship study", Biochemical Pharmacology, vol. 82, No. 5, Jun. 2, 2011, pp. 535-547, XP055144970.

Wang, et al: "Simple Procedure for the Synthesis of Arylmethylenemalononitrile Without Catalyst", Synthetic Communications, vol. 35, No. 14, Aug. 16, 2006 (Aug. 16, 2006), pp. 1915-1920, XP055938940.

International Search Report (PCT/ISA/210) and Written Opinion (PCT/ISA/237) mailed on Nov. 28, 2019, by the Canadian Patent Office as the International Searching Authority for International Application No. PCT/CA2019/051415.

Office Action (Notification of the First Office Action) issued on Feb. 8, 2023 by the China National Intellectual Property Office in corresponding Chinese Patent Application No. 201980062375.1, and an English Translation of the Office Action. (59 pages).

Office Action issued on Jan. 17, 2023 by the Intellectual Property India, Government of India in corresponding Indian Patent Application No. 202117011712, and an English Translation of the Office Action. (5 pages).

Guillot, S. L., et al."Thermal and Hydrolytic Decomposition Mechanisms of Organosilicon Electrolytes with Enhanced Thermal Stability for Lithium-Ion Batteries" Journal of The Electrochemical Society, vol. 164, No. 9, pp. A1907-A1917, 2017.

* cited by examiner

ADDITIVES FOR ELECTROLYTES IN Li-IONS BATTERIES

FIELD OF THE INVENTION

The present invention relates generally to additives for Li-ion batteries. More specifically, the present invention relates to nitrile-based additives for use in association with the electrolyte in Li-ion batteries.

BACKGROUND OF THE INVENTION

Li-ion batteries are widely used as energy source, and the demand is increasing. Typically, such battery comprises a negative electrode or anode, a positive electrode or cathode, and an electrolyte provided between the two spaced-apart electrodes. The electrolyte may comprise organic molecules or polymers and generally also comprises a lithium salt such as $LiPF_6$, LiTFSI or LiFSI. Moreover, the electrolyte may comprise linear carbonates such as dimethyl carbonate (DMC), diethyl carbonate (DEC), ethylmethyl carbonate (EMC) or cyclic carbonates such as ethylene carbonate (EC), propylene carbonate (PC) and butylene carbonate (BC).

Various studies related to the nature and composition of electrolytes and aimed at improving the performance and safety of Li-ion batteries, are reported in the art. For example, the use of additives comprising one or more nitrile groups is reported [1-3]. Indeed, it is known in the art that organic compounds comprising nitrile groups present good electrochemical properties and stability at high voltage and temperature.

There is still a need for methods of improving the performance and safety of Li-ion batteries. In particular, there is a need for nitrile-based organic compounds for use as additives in electrolytes.

SUMMARY OF THE INVENTION

The inventors have designed and prepared an additive for use in association with the electrolyte in a Li-ion battery. The additive of the invention is an organic compound as described herein below and which comprises at least one nitrile group. The organic compound is compatible with the electrolyte as well as other components of the battery.

The invention thus provides the following in accordance with aspects thereof:

(1) A method of improving the performance and safety of a Li-ion battery, comprising using a nitrile-based organic compound in association with the electrolyte of the battery, wherein the compound has a general formula I outlined below

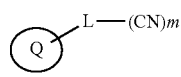

I wherein:
Q is a 5 to 12-member ring or bicycle ring, optionally the ring comprises one or more heteroatom which are the same or different and selected from the group consisting of N, O and S; preferably Q is a 5-10-, or a 5-, or a 6-member ring or bicycle ring;
L is present or absent and is a linker comprising one or more of alkyl, alkene and alkyne groups; and
m in an integer from 1 to 10, or 1 to 6, or 1 to 5, or 1 to 4, or 1 to 3.

(2) A method of improving the performance and safety of a Li-ion battery, comprising using a nitrile-based organic compound in association with the electrolyte of the battery, wherein the compound has a general formula II outlined below

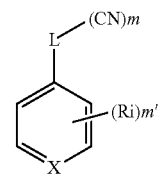

II wherein:
X is C or N;
L is present or absent and is a linker comprising one or more of alkyl, alkene and alkyne groups;
Ri each independently selected from the group consisting of H, alkyl, cycloalkyl, alkene, alkyne, aryl and alkylaryl, alkoxy, thioalkoxy, OH, SH, $NH_2$, a halogen atom, a halogeno alkyl, a halogeno alkoxy, a halogeno thioalkoxy, a cyano alkyl, a cyano alkene, a cyano alkyne, CN, $NO_2$, $SO_2$, COOH and acyloxycarbonyl; preferably selected from the group consisting of H, alkyloxy, halogen, halogeno alkyl, nitro, and cyano; more preferably selected from the group consisting of H, halogen, nitro and cyano;
m is an integer from 1 to 5, or 1 to 4, or 1 to 3; and
m' is an integer from 0 to 5, or 0 to 4, or 0 to 3, or 1 to 5, or 1 to 4, or 1 to 3.

(3) A method of improving the performance and safety of a Li-ion battery, comprising using a nitrile-based organic compound in association with the electrolyte of the battery, wherein the compound has a general formula III outlined below

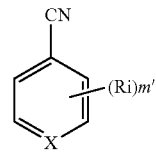

III wherein:
X is C or N;
Ri are each independently selected from the group consisting of H, alkyl, cycloalkyl, alkene, alkyne, aryl and alkylaryl, alkoxy, thioalkoxy, OH, SH, $NH_2$, a halogen atom, a halogeno alkyl, a halogeno alkoxy, a halogeno thioalkoxy, a cyano alkyl, a cyano alkene, a cyano alkyne, CN, $NO_2$, $SO_2$, COOH and acyloxycarbonyl; preferably Ri are each independently selected from the group consisting of H, alkyloxy, halogen, halogeno alkyl, nitro, and cyano; more preferably selected from the group consisting of H, halogen, nitro and cyano; and
m' is an integer from 0 to 5, or 0 to 4, or 0 to 3, or 1 to 5, or 1 to 4, or 1 to 3.

(4) A method of improving the performance and safety of a Li-ion battery, comprising using a nitrile-based organic compound in association with the electrolyte of the battery, wherein the compound has a general formula IV outlined below

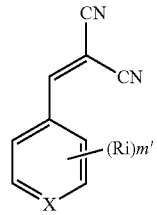

IV wherein:

X is C or N;

Ri are each independently selected from the group consisting of H, alkyl, cycloalkyl, alkene, alkyne, aryl and alkylaryl, alkoxy, thioalkoxy, OH, SH, NH₂, a halogen atom, a halogeno alkyl, a halogeno alkoxy, a halogeno thioalkoxy, a cyano alkyl, a cyano alkene, a cyano alkyne, CN, NO₂, SO₂, COOH and acyloxycarbonyl; preferably selected from the group consisting of H, alkyloxy, halogen, halogeno alkyl, nitro and cyano; more preferably selected from the group consisting of H, halogen, nitro and cyano; and m' is an integer from 0 to 5, or 0 to 4, or 0 to 3, or 1 to 5, or 1 to 4, or 1 to 3.

(5) A method of improving the performance and safety of a Li-ion battery, comprising using a nitrile-based organic compound in association with the electrolyte of the battery, wherein the compound has a general formula A outlined below

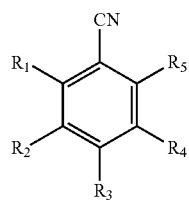

A wherein: $R_1$ to $R_5$ are each independently selected from the group consisting of H, alkyl, cycloalkyl, alkene, alkyne, aryl and alkylaryl, alkoxy, thioalkoxy, OH, SH, NH₂, a halogen atom, a halogeno alkyl, a halogeno alkoxy, a halogeno thioalkoxy, a cyano alkyl, a cyano alkene, a cyano alkyne, CN, NO₂, SO₂, COOH and acyloxycarbonyl; preferably $R_1$ to $R_5$ are each independently selected from the group consisting of H, alkyloxy, halogen, halogeno alkyl, nitro and cyano; more preferably selected from the group consisting of H, halogen, nitro and cyano.

(6) A method of improving the performance and safety of a Li-ion battery, comprising using a nitrile-based organic compound in association with the electrolyte of the battery, wherein the compound has a general formula B outlined below

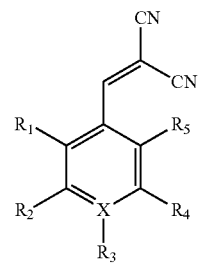

B wherein:

X is C and $R_3$ is H; or X is N; and $R_1$ to $R_5$ are each independently selected from the group consisting of H, alkyl, cycloalkyl, alkene, alkyne, aryl and alkylaryl, alkoxy, thioalkoxy, OH, SH, NH₂, a halogen atom, a halogeno alkyl, a halogeno alkoxy, a halogeno thioalkoxy, a cyano alkyl, a cyano alkene, a cyano alkyne, CN, NO₂, SO₂, COOH and acyloxycarbonyl; preferably $R_1$ to $R_5$ are each independently selected from the group consisting of H, alkyloxy, halogen, halogeno alkyl, nitro and cyano; more preferably selected from the group consisting of H, halogen, nitro and cyano.

(7) A method of improving the performance and safety of a Li-ion battery, comprising using a nitrile-based organic compound in association with the electrolyte of the battery, wherein the compound is A1, A2, A3 or A4 outlined below

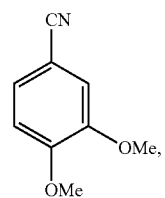

A1

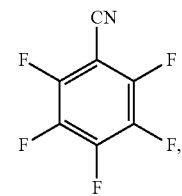

A2

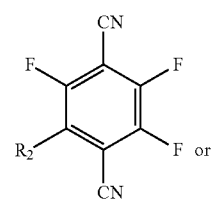

A3

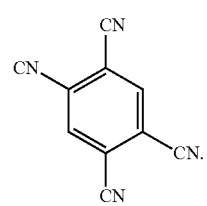

A4

(8) A method of improving the performance and safety of a Li-ion battery, comprising using a nitrile-based organic compound in association with the electrolyte of the battery, wherein the compound is B1, B2, B3, B4, B5, B6, B7 or B8 outlined below

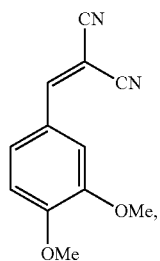

B1

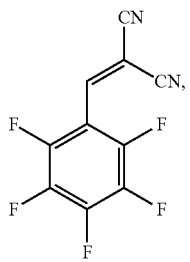

B2

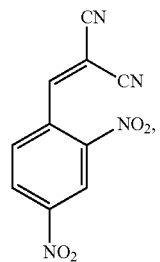

B3

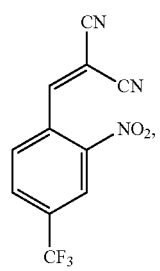

B4

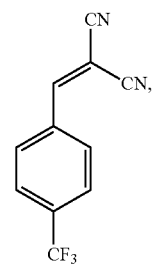

B5

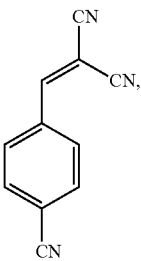

B6

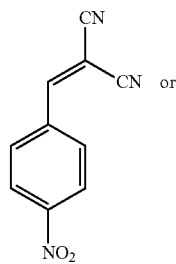

B7

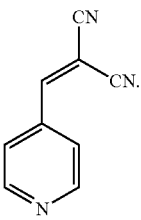

B8

(9) A method of improving the performance and safety of a Li-ion battery, comprising using a nitrile-based organic compound in association with the electrolyte of the battery, wherein the compound has a general formula V outlined below

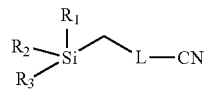

V wherein:
L is present or absent and is a linker comprising one of more of alkyl, alkene and alkyne groups; and
$R_1$ to $R_3$ are each independently alkyl groups; preferably C1 to C6 or C1 to C3 alkyl groups; more preferably at least one of $R_1$ to $R_3$ is $CH_3$, or each of $R_1$ to $R_3$ is $CH_3$.

(10) A method of improving the performance and safety of a Li-ion battery, comprising using a nitrile-based organic compound in association with the electrolyte of the battery, wherein the compound has a general formula VI outlined below

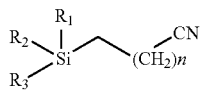

VI wherein:
n is an integer from 0 to 6, or 0 to 5, or 0 to 4, or 0 to 3, or 0 to 2; preferably n is an integer from 0 to 3; more preferably n is 0 or 1; and $R_1$ to $R_3$ are each independently alkyl groups; preferably C1 to C6 or C1 to C3 alkyl groups; more preferably at least one of $R_1$ to $R_3$ is $CH_3$, or each of $R_1$ to $R_3$ is $CH_3$.

(11) A method of improving the performance and safety of a Li-ion battery, comprising using a nitrile-based organic compound in association with the electrolyte of the battery, wherein the compound has a general formula C outlined below

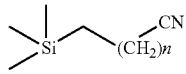

C wherein n is an integer from 0 to 6, or 0 to 5, or 0 to 4, or 0 to 3, or 0 to 2; preferably n is an integer from 0 to 3; more preferably n is 0 or 1.

(12) A method of improving the performance and safety of a Li-ion battery, comprising using a nitrile-based organic compound in association with the electrolyte of the battery, wherein the compound is C1 or C2 outlined below

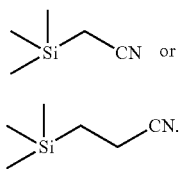

C1

C2

(13) A method of improving the performance and safety of a Li-ion battery, comprising using a nitrile-based organic compound in association with the electrolyte of the battery, wherein the compound has a general formula IX outlined below

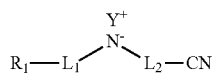

IX wherein:
$R_1$ is CN or $CH_3$;
$L_1$ and $L_2$ are each independently present or absent and are each independently a linker comprising alkyl, alkene and/or alkyne groups; and
Y is Na, K or Li; preferably Y is Na.

(14) A method of improving the performance and safety of a Li-ion battery, comprising using a nitrile-based organic compound in association with the electrolyte of the battery, wherein the compound has a general formula X outlined below

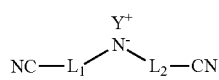

X wherein:
$L_1$ and $L_2$ are each independently present or absent and are each independently a linker comprising one or more of alkyl, alkene and alkyne groups; and
Y is Na, K or Li; preferably Y is Na.

(15) A method of improving the performance and safety of a Li-ion battery, comprising using a nitrile-based organic compound in association with the electrolyte of the battery, wherein the compound has a general formula XI outlined below

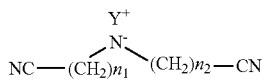

XI wherein:
n1 and n2 are each independently an integer from 0 to 10, or 0 to 6, or 0 to 3; preferably at least one of n1 and n2 is 0, or both n1 and n2 are 0; and
Y is Na, K or Li; preferably Y is Na.

(16) A method of improving the performance and safety of a Li-ion battery, comprising using a nitrile-based organic compound in association with the electrolyte of the battery, wherein the compound has a general formula D outlined below

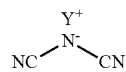

D wherein Y is Na, K or Li; preferably Y is Na.

(17) A method of improving the performance and safety of a Li-ion battery, comprising using a nitrile-based organic compound in association with the electrolyte of the battery, wherein the compound has a general formula D1 outlined below

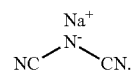

D1

(18) A compound having a general formula VII outlined below

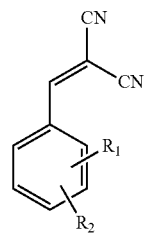

VII wherein $R_1$ and $R_2$ are each independently selected from the group consisting of H, alkyl, cycloalkyl, alkene, alkyne, aryl and alkylaryl, alkoxy, thioalkoxy, OH, SH, $NH_2$, a halogen atom, a halogeno alkyl, a halogeno alkoxy, a halogeno thioalkoxy, a cyano alkyl, a cyano alkene, a cyano alkyne, CN, $NO_2$, $SO_2$, COOH and acyloxycarbonyl; preferably selected from the group consisting of H, alkyloxy, halogen, halogeno alkyl, nitro and cyano; more preferably selected from the group consisting of H, halogen, nitro and cyano.

(19) A compound having a general formula VIII outlined below

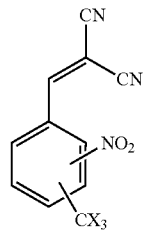

wherein X is a halogen atom; preferably X is F.

(20) A compound of formula B4 outlined below

B4

[Structure: 2-(2-nitro-4-trifluoromethylbenzylidene)malononitrile with CN, CN, NO2, CF3 groups]

(21) A method of improving the performance and safety of a Li-ion battery, comprising using a nitrile-based organic compound in association with the electrolyte of the battery, wherein the compound as defined in any one of (18) to (20) above.

(22) The method according to any one of (1) to (17) and (21) above, wherein the nitrile-based organic compound is added to the electrolyte; optionally an amount of the additive (nitrile-based organic compound) is between about 0.01 to about 5.0% wt, or about 0.01 to about 3.0% wt, or about 0.01 to about 1.0% wt, or about 0.05 to about 1.0% wt, or about 0.1 to about 1.0% wt, about 0.1 to about 0.8% wt, or about 0.1 to about 0.5% wt, or about 0.1 to about 0.3% wt, is 0.1% wt, or is 0.5% wt.

(23) An electrolyte comprising a compound which is selected from the group consisting of: I, II, III, IV, A, B, A1, A2, A3, A4, B1, B2, B3, B4, B5, B6, B7, B8, V, VI, C, C1, C2, IX, X, XI, D, and D1 as defined in any one of the methods of (1) to (17) above.

(24) An electrolyte comprising the compound as defined in any one of (18) to (20) above.

(25) A battery comprising the electrolyte as defined in (23) or (24) above.

(26) An additive for an electrolyte for use in a Li-ion battery, comprising a compound which is selected from the group consisting of: I, II, III, IV, A, B, A1, A2, A3, A4, B1, B2, B3, B4, B5, B6, B7, B8, V, VI, C, C1, C2, IX, X, XI, D, and D1 as defined in any one of the methods of (1) to (17) above.

(27) An additive for an electrolyte for use in a Li-ion battery, comprising a compound as defined in any one of (18) to (20) above.

(28) The method, electrolyte, battery or additive according to any one of (1) to (27) above, wherein the Li-ion battery is a battery wherein the cathode comprises a lithium-containing material;

(29) The method, electrolyte, battery or additive according to any one of (1) to (27) above, wherein the Li-ion battery is a battery wherein the cathode comprises lithium cobalt oxide (LCO), lithium manganese oxide (LMO), lithium nickel oxide (LNO) and the like including olivines, lithium oxides, nickel manganese cobalt oxide (NMC).

(30) The method, electrolyte, battery or additive according to (28) or (30) above, wherein the performance (capacity, reversibility) of the battery is improved.

Other objects, advantages and features of the present invention will become more apparent upon reading of the following non-restrictive description of specific embodiments thereof, given by way of example only with reference to the accompanying drawings.

DESCRIPTION OF ILLUSTRATIVE EMBODIMENTS

Figure 1:
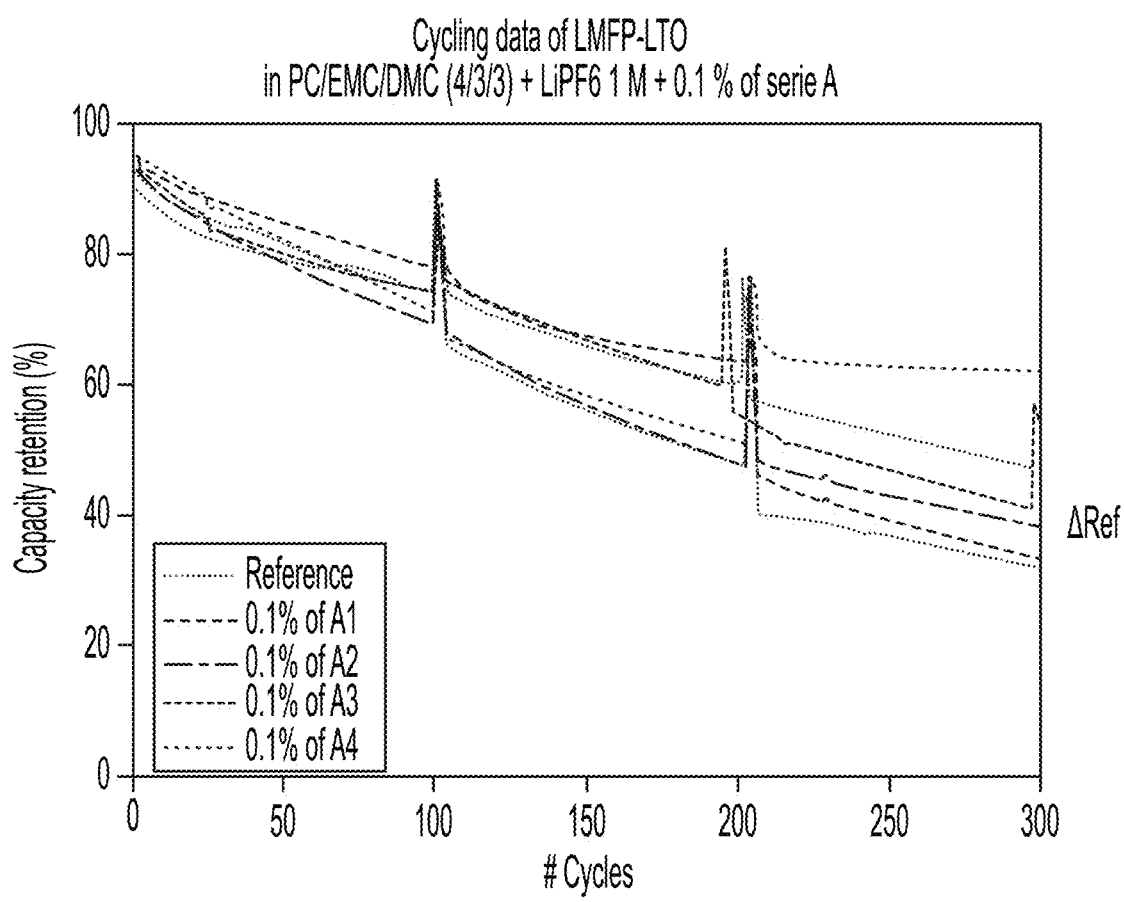
FIG. 1: Cycling data of LMFP-LTO battery (PC/EMC/DMC (4/3/3)+1M LiPF$_6$+0.1 wt % additive according to the invention (a compounds of Serie A)) versus Reference after 300 cycles at 45° C.

Before the present invention is further described, it is to be understood that the invention is not limited to the particular embodiments described below, as variations of these embodiments may be made and still fall within the scope of the appended claims. It is also to be understood that the terminology employed is for the purpose of describing particular embodiments, and is not intended to be limiting. Instead, the scope of the present invention will be established by the appended claims.

In order to provide a clear and consistent understanding of the terms used in the present specification, a number of definitions are provided below. Moreover, unless defined otherwise, all technical and scientific terms as used herein have the same meaning as commonly understood to one of ordinary skill in the art to which this disclosure pertains.

The use of the word "a" or "an" when used in conjunction with the term "comprising" in the claims and/or the specification may mean "one", but it is also consistent with the meaning of "one or more", "at least one", and "one or more than one". Similarly, the word "another" may mean at least a second or more.

As used in this specification and claim(s), the words "comprising" (and any form of comprising, such as "comprise" and "comprises"), "having" (and any form of having, such as "have" and "has"), "including" (and any form of including, such as "include" and "includes") or "containing" (and any form of containing, such as "contain" and "contains"), are inclusive or open-ended and do not exclude additional, unrecited elements or process steps.

As used herein when referring to numerical values or percentages, the term "about" includes variations due to the methods used to determine the values or percentages, statistical variance and human error. Moreover, each numerical parameter in this application should at least be construed in light of the number of reported significant digits and by applying ordinary rounding techniques.

Term "alkyl" or "alk" as used herein, represents a monovalent group derived from a straight or branched chain saturated hydrocarbon comprising, unless otherwise specified, from 1 to 15 carbon atoms and is exemplified by methyl, ethyl, n- and iso-propyl, n-, sec-, iso- and tert-butyl, neopentyl and the like and may be optionally substituted with one, two, three or, in the case of alkyl groups comprising two carbons or more, four substituents.

The term "alkoxy" or "alkyloxy" as used interchangeably herein, represents an alkyl group attached to the parent molecular group through an oxygen atom.

The term "alkylthio" or "thioalkoxy" as used interchangeably herein, represents an alkyl group attached to the parent molecular group through a sulfur atom.

The term "alkylene" as used herein, represents a saturated divalent hydrocarbon group derived from a straight or branched chain saturated hydrocarbon by the removal of two hydrogen atoms, and is exemplified by methylene, ethylene, isopropylene and the like.

The term "alkenyl" as used herein, represents monovalent straight or branched chain groups of, unless otherwise specified, from 2 to 15 carbons, such as, for example, 2 to 6 carbon atoms or 2 to 4 carbon atoms, containing one or more carbon-carbon double bonds and is exemplified by ethenyl, 1-propenyl, 2-propenyl, 2-methyl-1-propenyl, 1-butenyl, 2-butenyl and the like and may be optionally substituted with one, two, three or four substituents.

The term "alkynyl" as used herein, represents monovalent straight or branched chain groups of from two to six carbon atoms comprising a carbon-carbon triple bond and is exemplified by ethynyl, 1-propynyl, and the like and may be optionally substituted with one, two, three or four substituents.

The term "cycloalkyl" as used herein, represents a monovalent saturated or unsaturated non-aromatic cyclic hydrocarbon group of three to eight carbon atoms, unless otherwise specified, and is exemplified by cyclopropyl, cyclobutyl, cyclopentyl, cyclohexyl, cycloheptyl, bicyclo[2.2.1]heptyl and the like.

The term "halogen" or "halo" as used interchangeably herein, represents F, Cl, Br and The term "heteroatom", as used herein, is understood as being oxygen, sulfur or nitrogen.

The inventors have designed and prepared an additive for use in association with the electrolyte in a Li-ion battery. The additive of the invention is an organic compound as described herein below and which comprises at least one nitrile group. Also, the organic compound is compatible with the electrolyte as well as other components of the battery.

More specifically, the additive of the invention for use in association with the electrolyte is a nitrile-based organic compound as described herein and having general formulae I-XI, A, B, C and D depicted below.

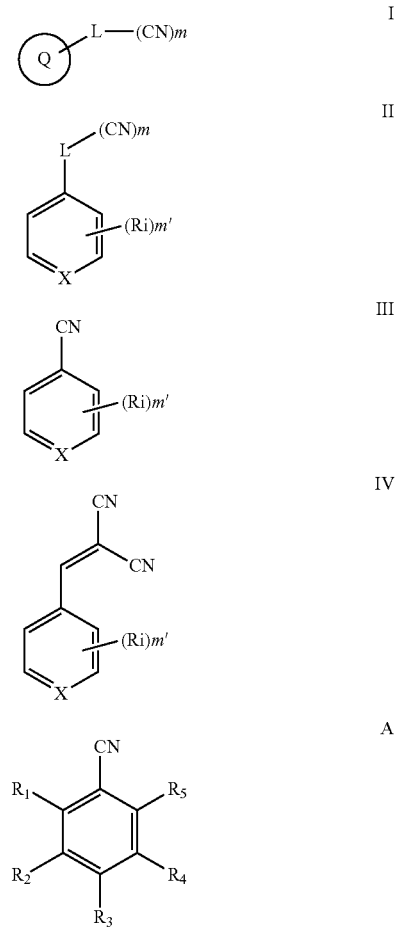

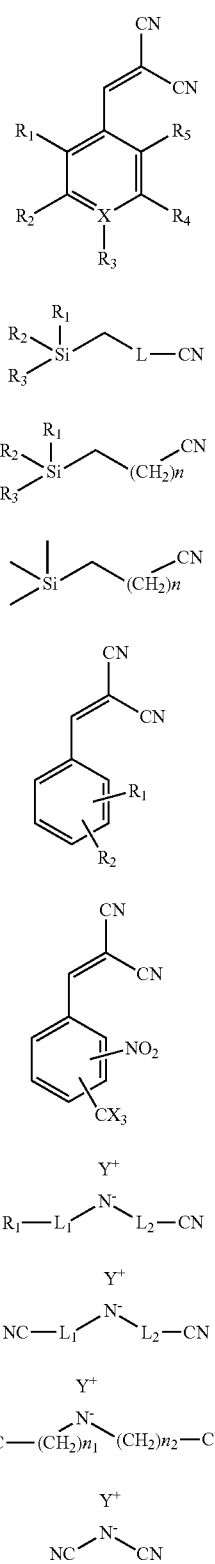

Such organic compounds are exemplified by compounds defined in Table 1 below, namely, Compounds A1-A4, B1-68, C1-C2 and D1.

TABLE 1

Organic compounds according to the invention (Series A, B, C and D)

| | | $R_1$ | $R_2$ | $R_3$ | $R_4$ | $R_5$ | X | n | | Cycle |
|---|---|---|---|---|---|---|---|---|---|---|
| A | A1 | H | H | OMe | OMe | H | | | 0.1% | 300 |
| | A2 | F | F | F | F | F | | | 0.1% | 300 |
| | A3 | F | F | CN | F | F | | | 0.1% | 300 |
| | A4 | CN | H | CN | CN | H | | | 0.1% | 300 |
| B | B1 | H | H | OMe | OMe | H | C | | 0.5% | 300 |
| | B2 | F | F | F | F | F | C | | 0.5% | 200 |
| | B3 | H | H | $NO_2$ | H | $NO_2$ | C | | 0.5% | poor results |
| | B4 | H | H | $CF_3$ | H | $NO_2$ | C | | 0.5% | 300 |
| | B5 | H | H | $CF_3$ | H | H | C | | 0.5% | 300 |
| | B6 | H | H | CN | H | H | C | | 0.5% | 300 |
| | B7 | H | H | $NO_2$ | H | H | C | | 0.5% | poor results |
| | B8 | H | H | H | H | H | N | | 0.5% | 300 |
| C | C1 | | | | | | | 0 | 0.5% | 300 |
| | C2 | | | | | | | 1 | 0.5% | 300 |
| D | D1 | | | | | | | | 0.5% | 300 |

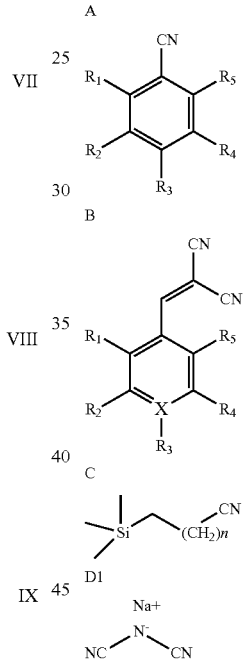

The present invention is illustrated in further details by the following non-limiting examples.

Nitrile-Based Organic Compounds for Use as Additive in Association with Li-Ion Electrolytes

Example 1—General Procedure for the Preparation of the Compounds

To a solution of aldehyde (1 eq.) in 15 mL of chloroform are added, molonodinitrile (1.5 eq.) and few drops of triethylamine. The mixture is refluxed one night under nitrogen. After return to room temperature, dichloromethane is added, and the solution is washed twice with water and dried over $MgSO_4$. After solvent removal, the residue is chromatographed (silica gel/dichloromethane) to give a solid.

Example 2—Compound B1

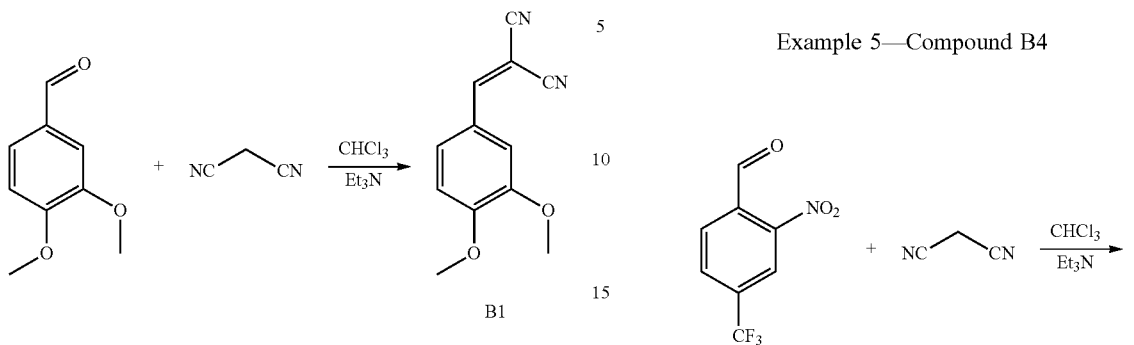

Bright yellow solid (70%). NMR $^1$H (400 MHz, CDCl$_3$) δ: 7.69 (d, 1H, J=4 Hz); 7.64 (s, 1H); 7.38 (dd, 1H, J=4 Hz, J=12 Hz); 6.95 (d, 1H, J=12 Hz); 3.99 (s, 3H); 3.93 (s, 3H).

Example 3—Compound B2

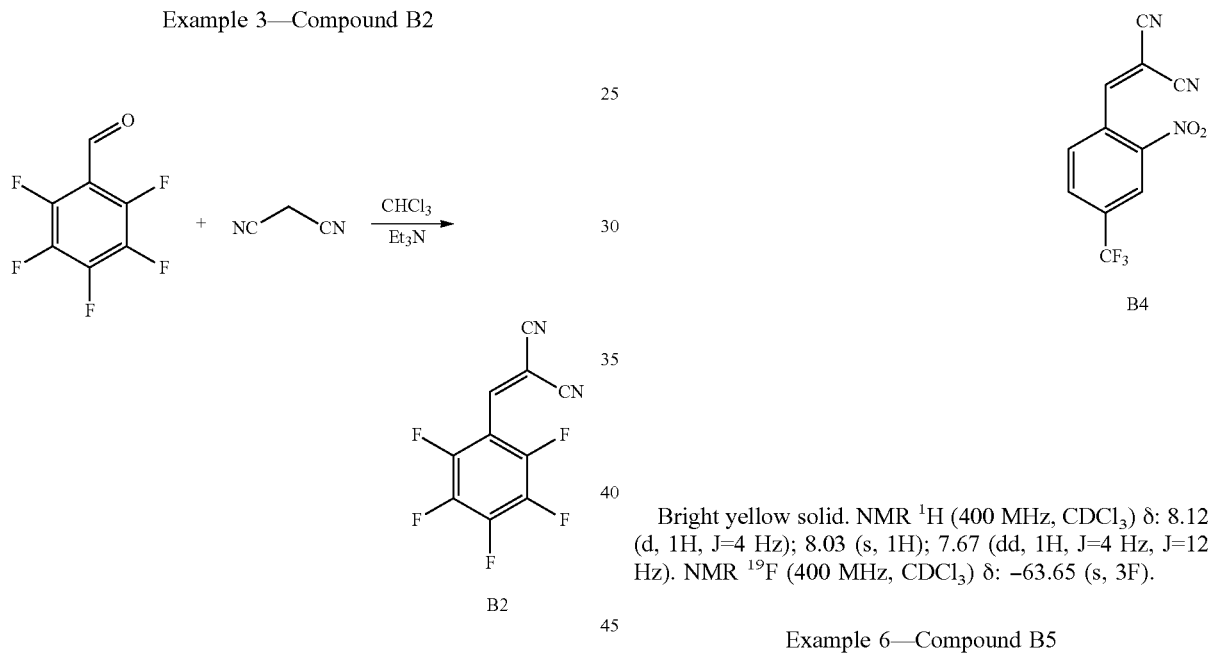

Yellow solid (40%). NMR $^1$H (400 MHz, CDCl$_3$) δ: 7.77 (s, 1H). NMR $^{19}$F (400 MHz, CDCl$_3$) δ: −132.55 (s, 2H); −143.68 (s, 1H); −158.50 (s, 1H).

Example 4—Compound B3

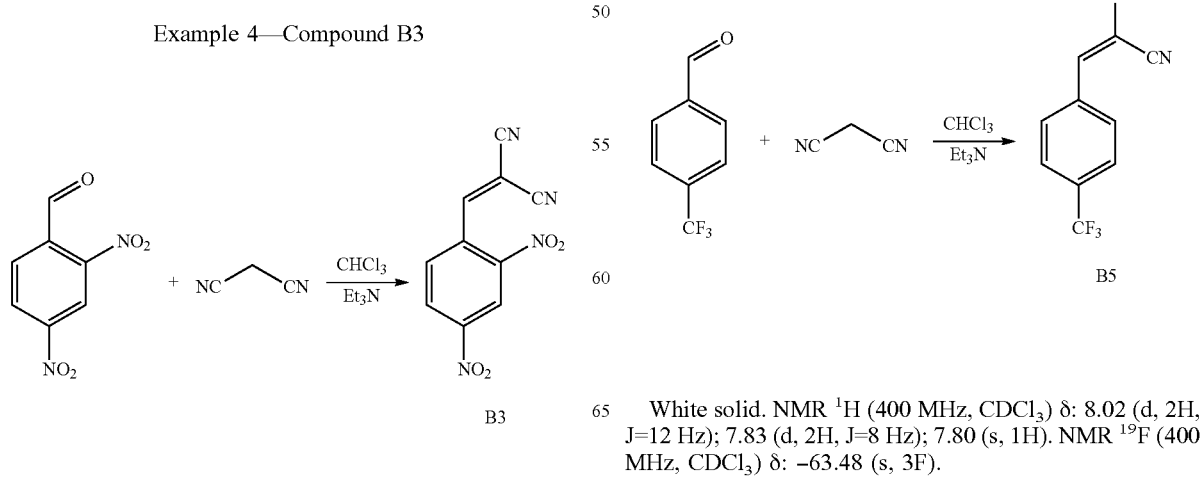

White solid. NMR $^1$H (400 MHz, CDCl$_3$) δ: 8.60 (d, 1H, J=4 Hz); 8.25 (dd, 1H, J=4 Hz, J=12 Hz); 8.18 (s, 1H); 8.15 (d, 1H, J=12 Hz).

Example 5—Compound B4

Bright yellow solid. NMR $^1$H (400 MHz, CDCl$_3$) δ: 8.12 (d, 1H, J=4 Hz); 8.03 (s, 1H); 7.67 (dd, 1H, J=4 Hz, J=12 Hz). NMR $^{19}$F (400 MHz, CDCl$_3$) δ: −63.65 (s, 3F).

Example 6—Compound B5

White solid. NMR $^1$H (400 MHz, CDCl$_3$) δ: 8.02 (d, 2H, J=12 Hz); 7.83 (d, 2H, J=8 Hz); 7.80 (s, 1H). NMR $^{19}$F (400 MHz, CDCl$_3$) δ: −63.48 (s, 3F).

Example 7—Compound B6

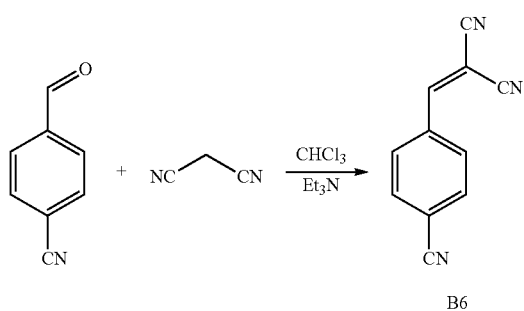

White solid. NMR $^1$H (400 MHz, CDCl$_3$) δ: 7.99 (d, 2H, J=8 Hz); 7.83 (d, 2H, J=8 Hz); 7.74 (s, 1H).

Example 8—Compound B7

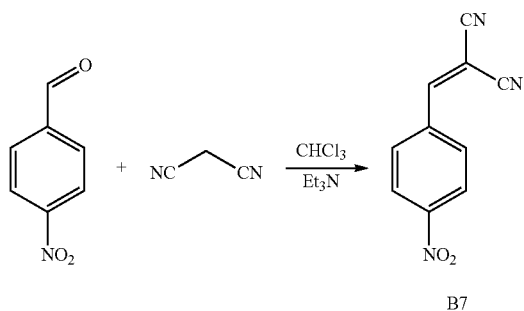

Pale orange solid. NMR $^1$H (400 MHz, CDCl$_3$) δ: 8.39 (d, 2H, J=12 Hz); 8.07 (d, 2H, J=8 Hz); 7.88 (s, 1H).

Example 9—Compound B8

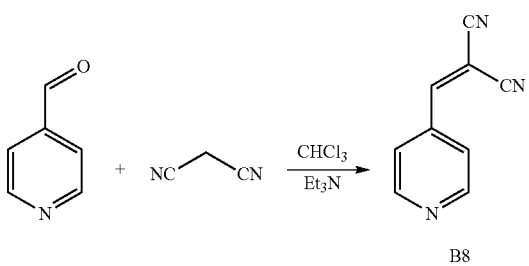

Pink solid. NMR $^1$H (400 MHz, CDCl$_3$) δ: 8.89 (d, 2H, J=12 Hz); 7.81 (s, 2H); 7.68 (d, 2H, J=8 Hz).

Compounds of the Series A and C and Compound D1 are commercially available and were used as received.

Figure 2:
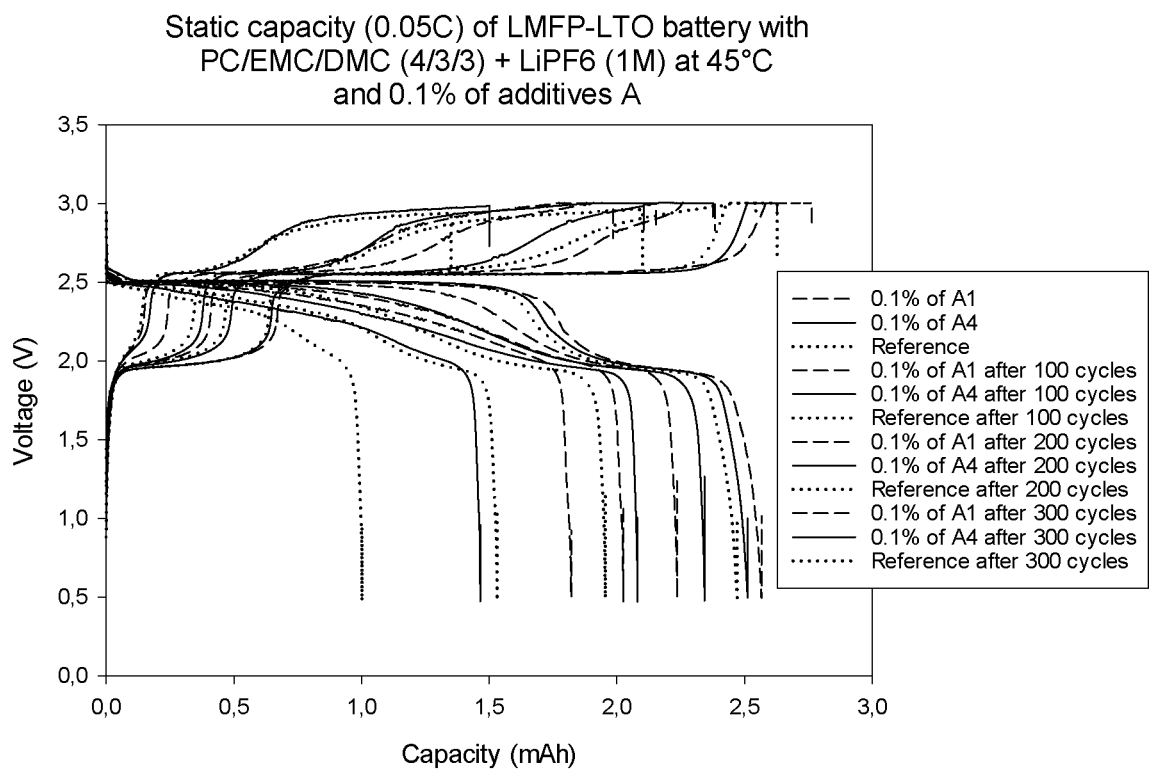
FIG. 2: Static capacity (0.05C) of LMFP-LTO battery (PC/EMC/DMC (4/3/3)+1M LiPF$_6$+0.1 wt % additive according to the invention (a compound of Serie A)) versus Reference at 45° C.
Figure 3:
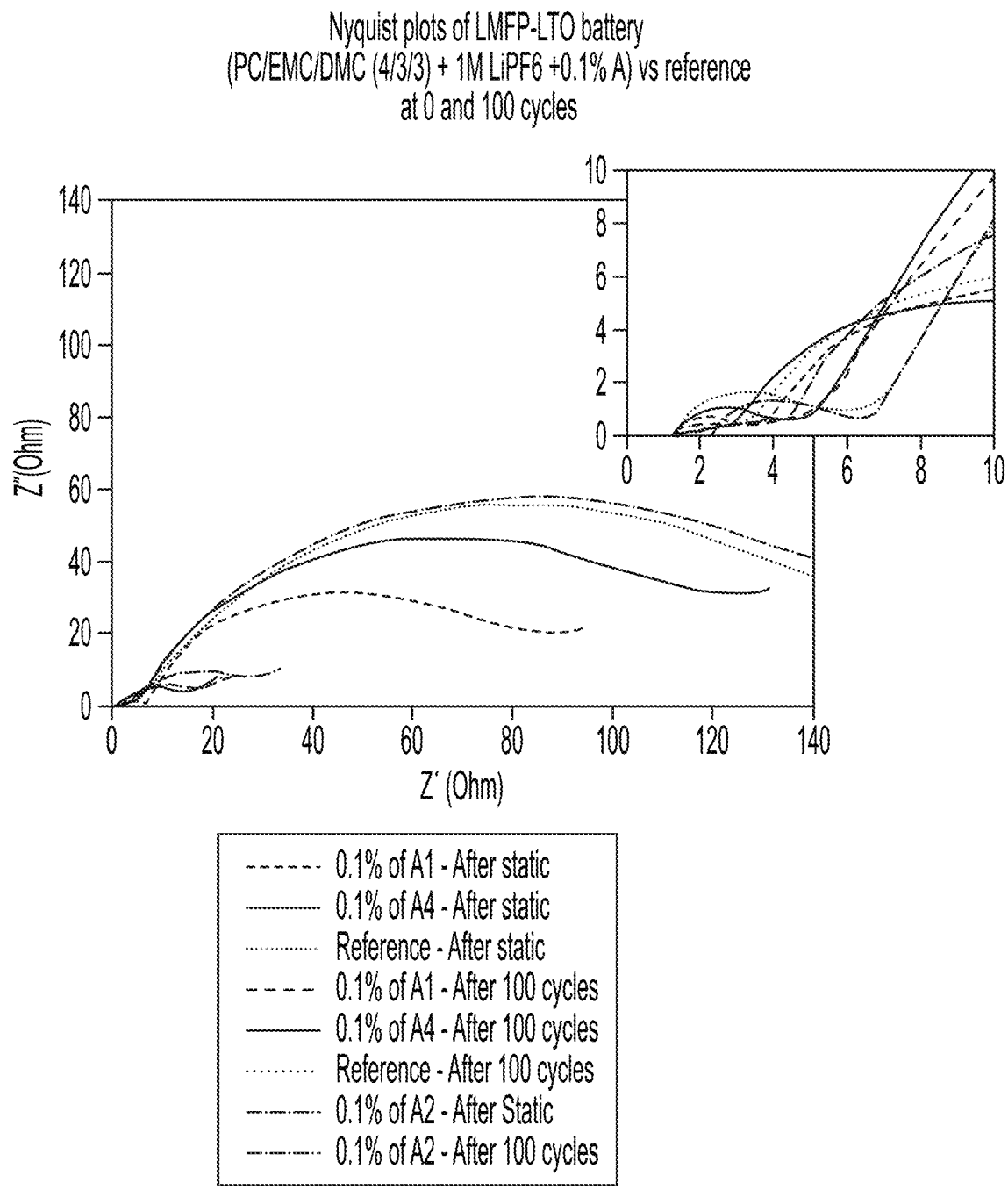
FIG. 3: Nyquist plots of LMFP-LTO battery (PC/EMC/DMC (4/3/3)+1M LiPF$_6$+0.1 wt % additive according to the invention (a compound of Serie A)) versus Reference, at 0 and 100 cycles.
Figure 4:
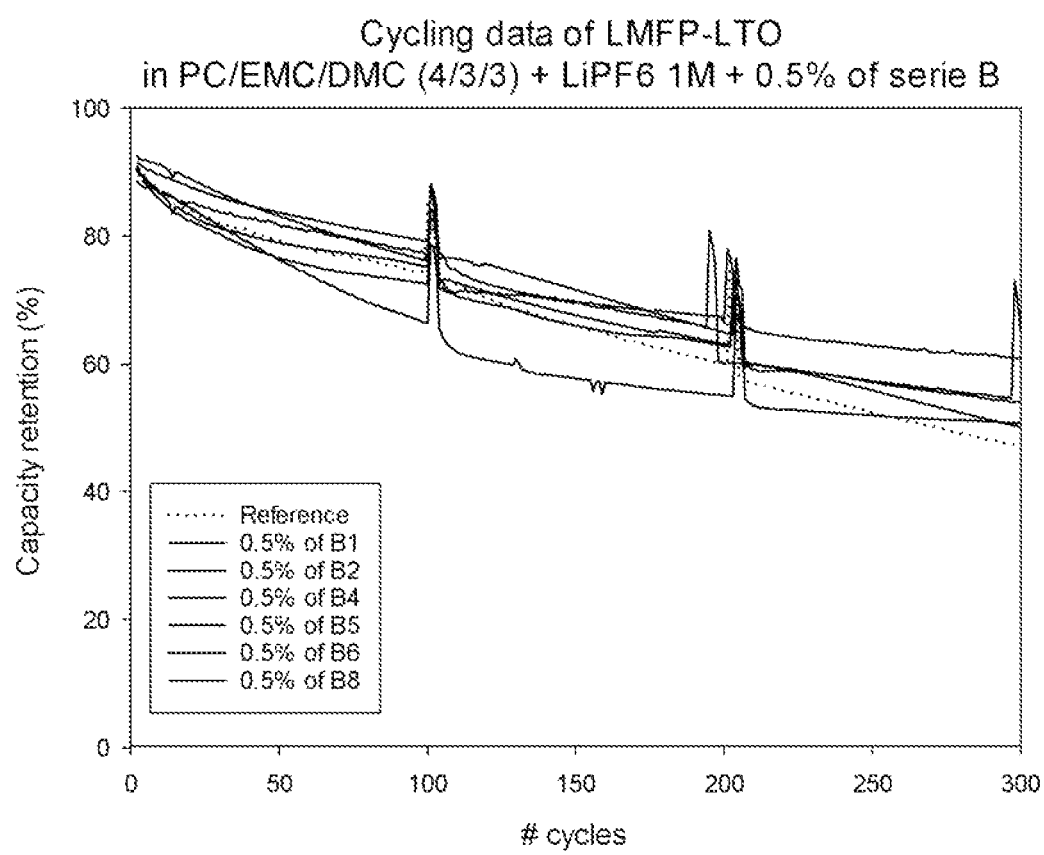
FIG. 4: Cycling data of LMFP-LTO battery (PC/EMC/DMC (4/3/3)+1M LiPF$_6$+0.5 wt % additive according to the invention (a compounds of Serie B)) versus Reference after 300 cycles at 45° C.
Figure 5:
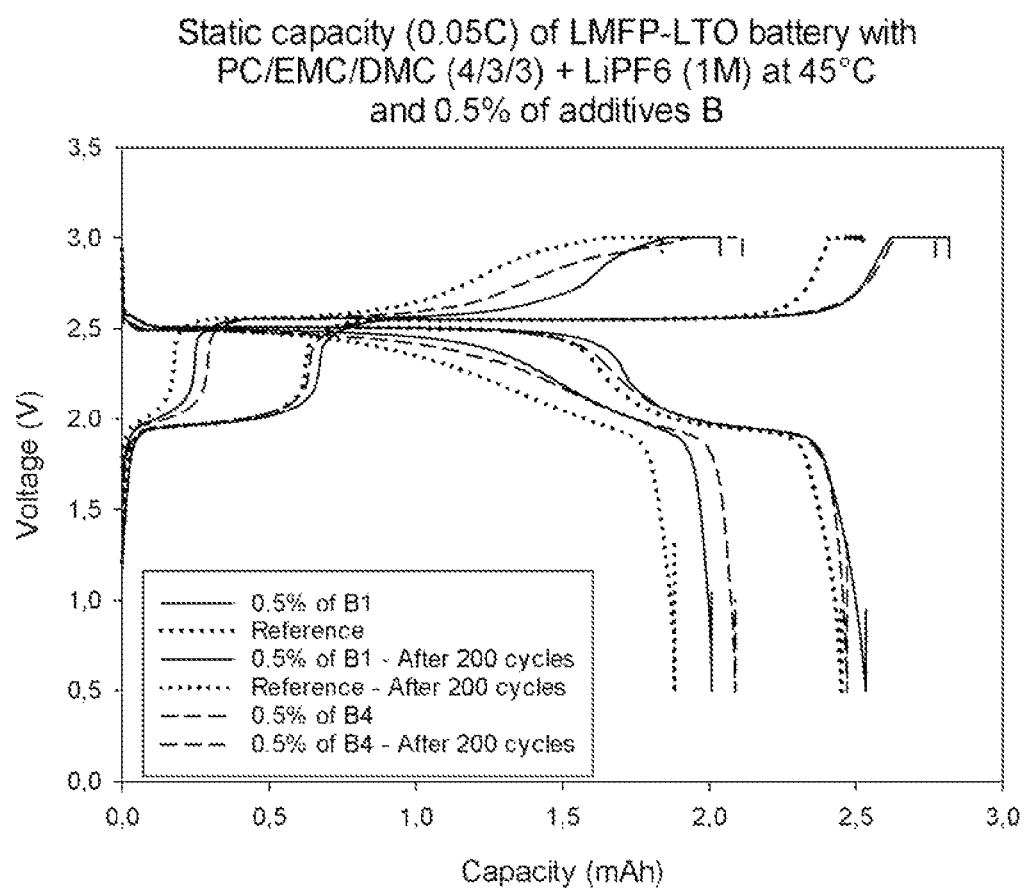
FIG. 5: Static capacity (0.05C) of LMFP-LTO battery (PC/EMC/DMC (4/3/3)+1M LiPF$_6$+0.5 wt % additive according to the invention (a compound of Serie B)) versus Reference at 45° C.
Figure 6:
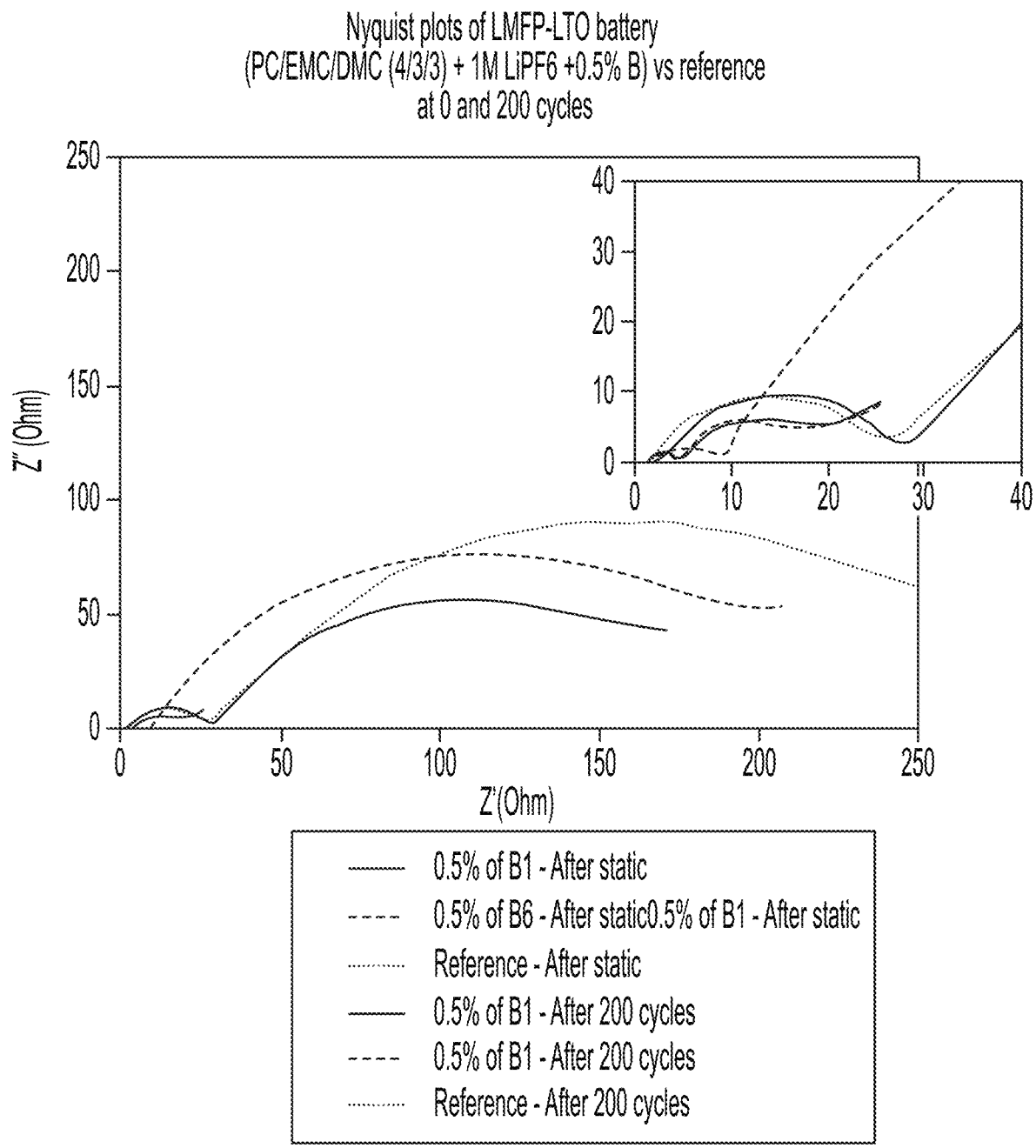
FIG. 6: Nyquist plots of LMFP-LTO battery (PC/EMC/DMC (4/3/3)+1M LiPF$_6$+0.5 wt % additive according to the invention (a compound of Serie B)) versus Reference, at 0 and 200 cycles.
Figure 7:
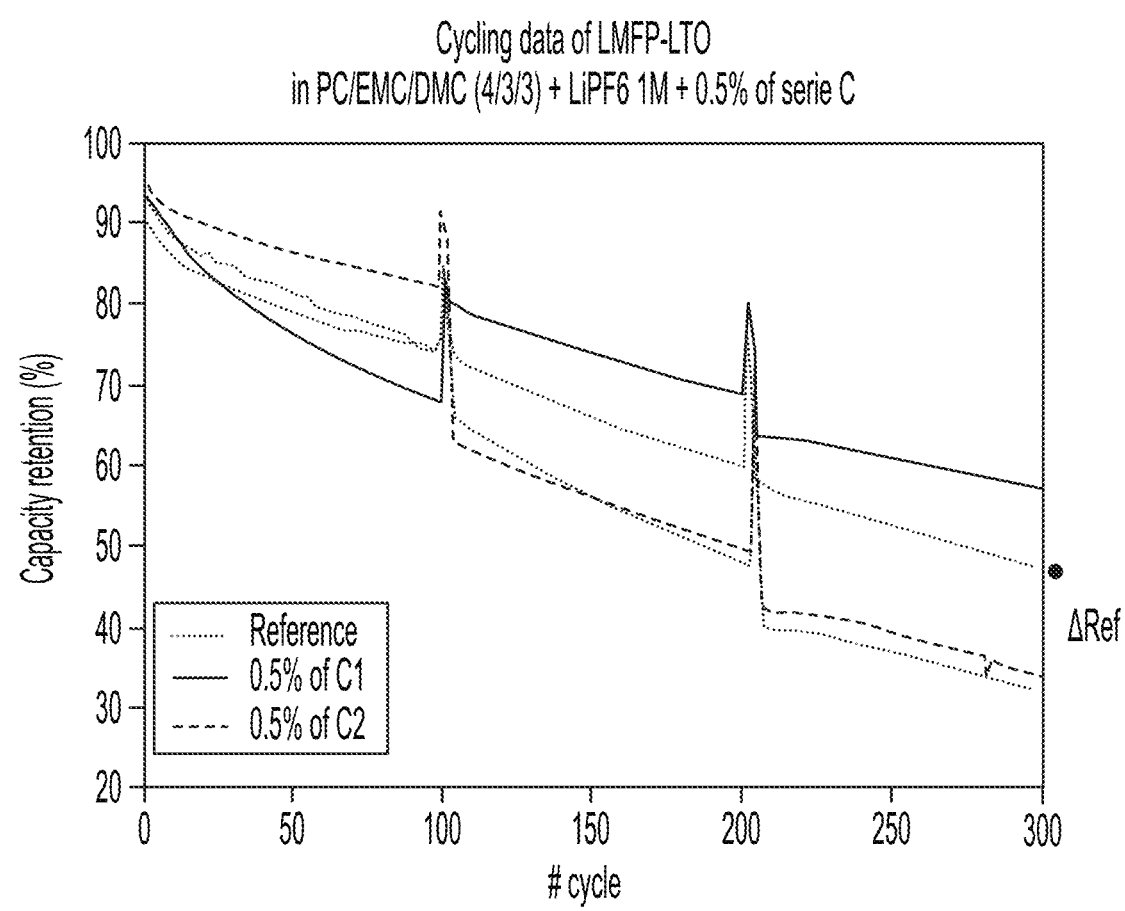
FIG. 7: Cycling data of LMFP-LTO battery (PC/EMC/DMC (4/3/3)+1M LiPF$_6$+0.5 wt % additive according to the invention (a compounds of Serie C)) versus Reference after 300 cycles at 45° C.
Figure 8:
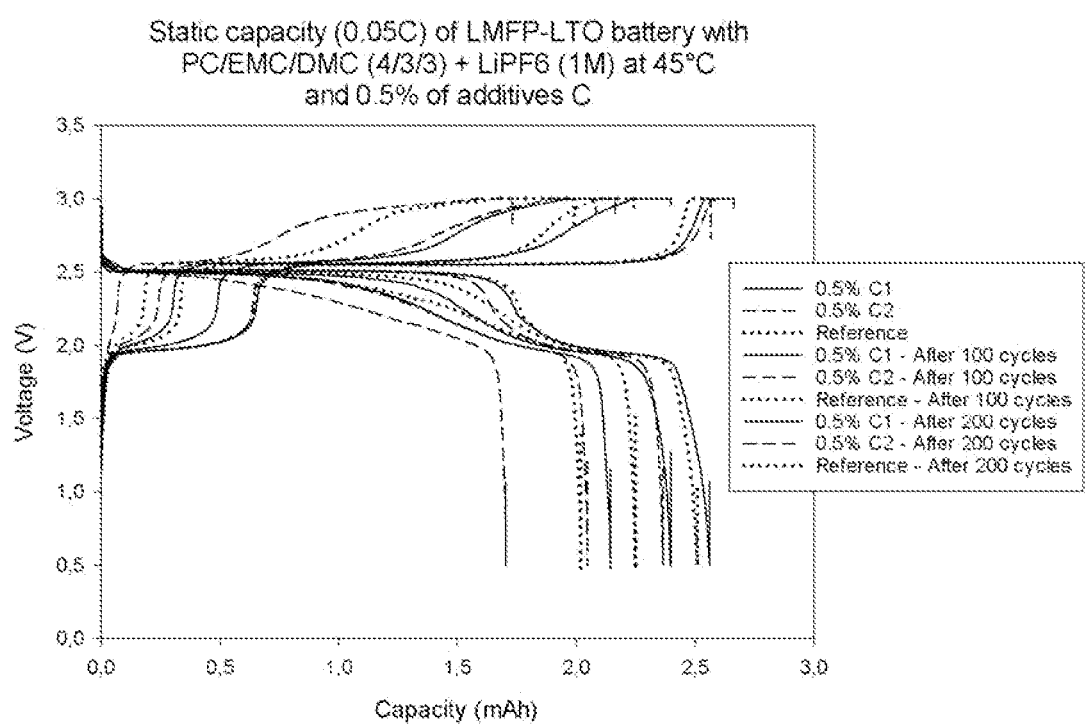
FIG. 8: Static capacity (0.05C) of LMFP-LTO battery (PC/EMC/DMC (4/3/3)+1M LiPF$_6$+0.5 wt % additive according to the invention (a compound of Serie C)) versus Reference at 45° C.
Figure 9:
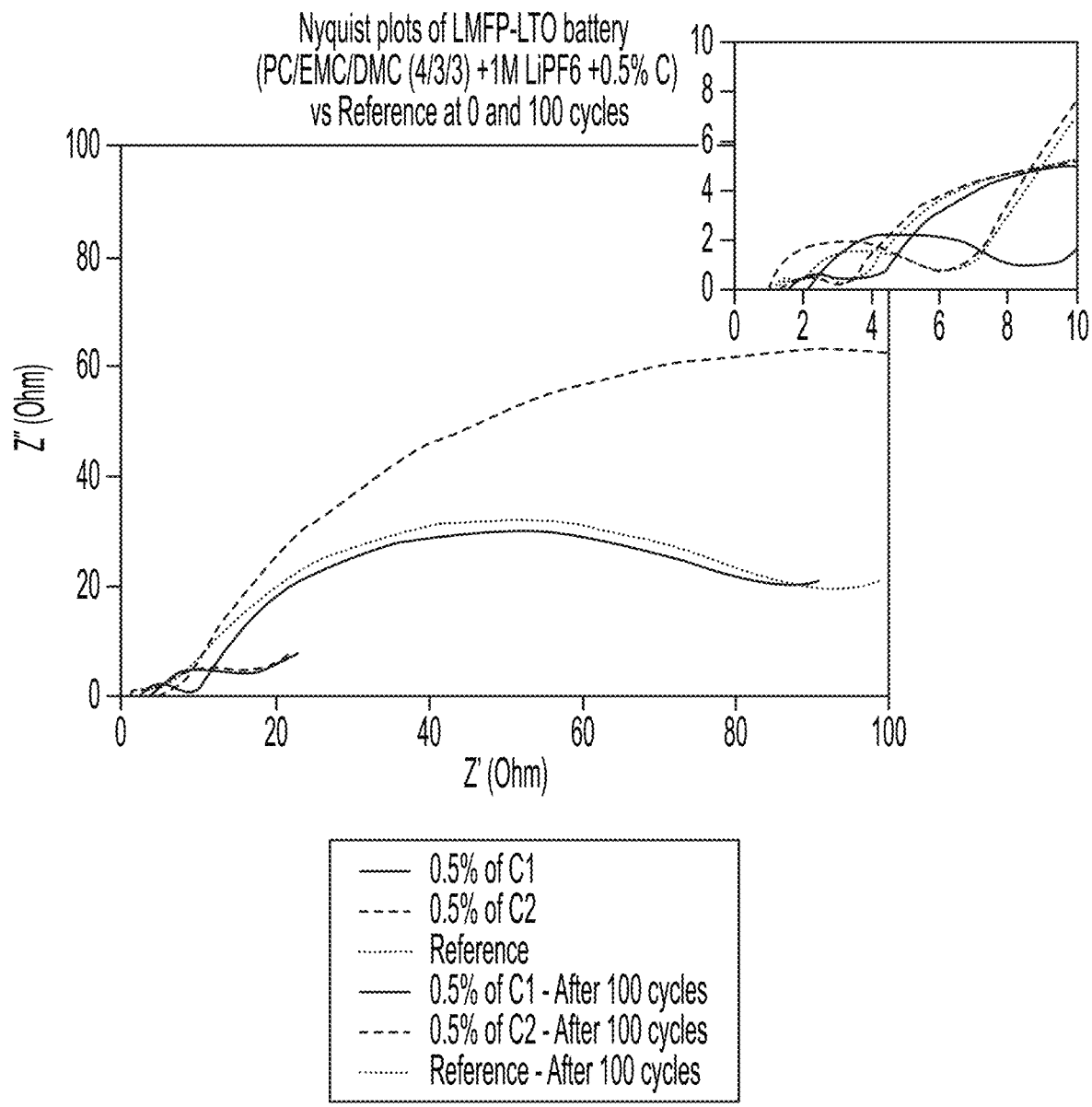
FIG. 9: Nyquist plots of LMFP-LTO battery (PC/EMC/DMC (4/3/3)+1M LiPF$_6$+0.5 wt % additive according to the invention (a compound of Serie C)) versus Reference, at 0 and 100 cycles.

Referring to the figures, FIGS. 1-3 outline results obtained using compounds of the Serie A; FIGS. 4-6 outline results obtained using compounds of the Serie B; FIGS. 7-9 outline results obtained using compounds of the Serie C; and FIGS. 10-11 outline results obtained using compounds of the Serie D. It should be noted that Reference batteries as well as batteries according to the invention, do not contain vinylene carbonate (VC), which explains the poor stability after 300 cycles. Nonetheless as can be seen, batteries comprising the additive according to the invention present a far better stability.

As can be seen in FIG. 2, use of 0.1 wt % of compound A1 or A4 allows for improvement of the battery capacity as well as a better reversibility. Moreover, a global decrease of the battery resistance is noted (FIG. 3).

FIG. 5 shows results obtained for compounds B1 and B4. Use of 0.5 wt % of the additive allows for an improvement of the battery capacity. A global decrease of the battery resistance is noted (FIG. 6).

FIG. 7 shows results obtained for compounds C1 and C2. Use of 0.5 wt % of the additive yields a good stability after 300 cycles at 45° C. As can be seen in FIG. 8, better results are obtained for compound C1 (shorter carbon chain).

Figure 10:
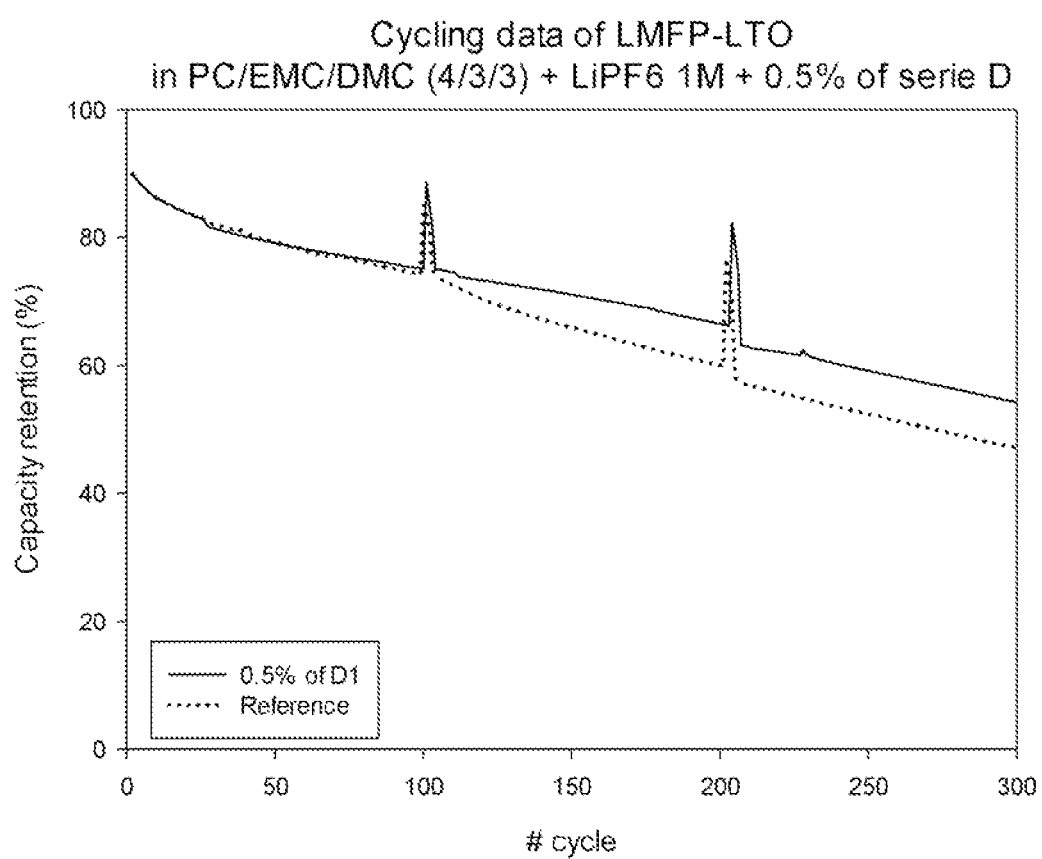
FIG. 10: Cycling data of LMFP-LTO battery (PC/EMC/DMC (4/3/3)+1M LiPF$_6$+0.5 wt % additive according to the invention (a compounds of Serie D)) versus Reference after 100 cycles at 45° C.
Figure 11:
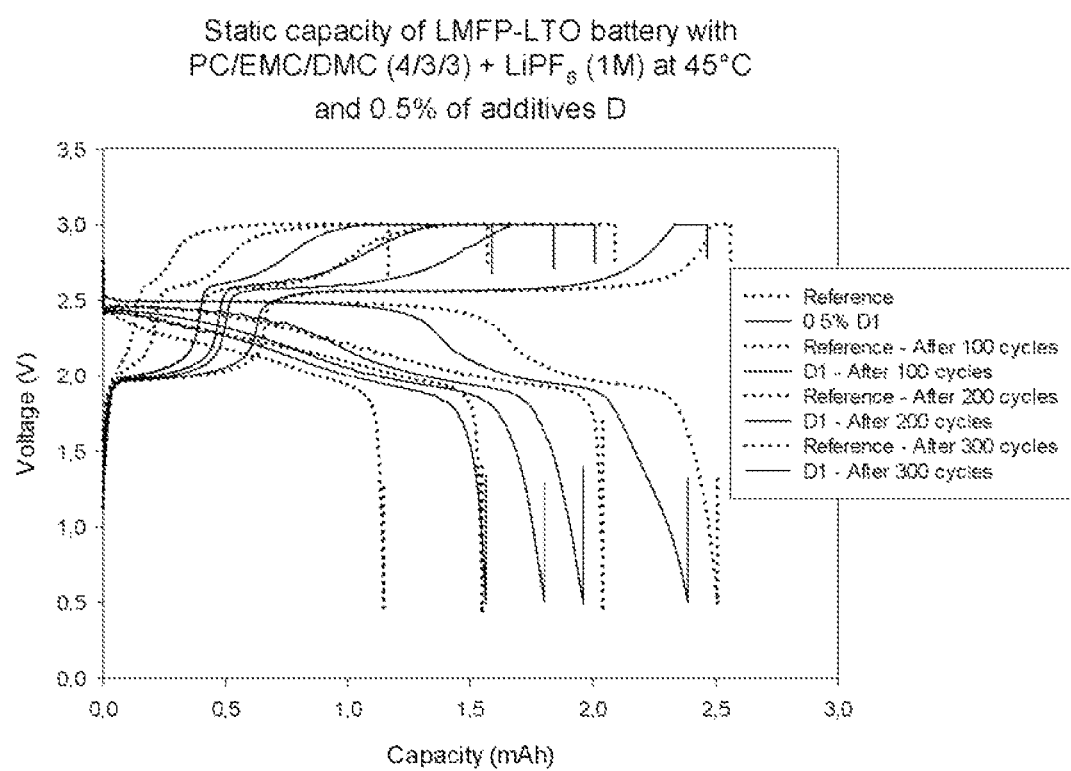
FIG. 11: Static capacity (0.05C) of LMFP-LTO battery (PC/EMC/DMC (4/3/3)+1M LiPF$_6$+0.5 wt % additive according to the invention (a compound of Serie D)) versus Reference at 45° C.

FIG. 10 shows results obtained for compound D1. As can be seen in FIG. 11, use of 0.5 wt % of compound D1 allows for improvement of the battery capacity as well as a better reversibility.

As will be understood by a skilled person, the additive for use in association with the electrolyte are adapted to be compatible with the components of the battery including the electrolyte and the cathode active material.

The invention is described in relation to lithium manganese iron phosphate (LMFP)—lithium titanium oxide (LTO) batteries. As will be understood by a skilled person, other lithium-ion batterie types may also be used. In other words, any battery wherein the cathode active material comprises a lithium-containing material may be used. Such lithium-containing material may be lithium cobalt oxide (LCO), lithium manganese oxide (LMO), lithium nickel oxide (LNO) and the like including olivines, lithium oxides, nickel manganese cobalt oxide (N M C).

Also, as will be understood by a skilled person, the anode material may be of any suitable type, such as for example lithium alloys, Si, SiOx, graphite and carbon mixtures, titanates, lithium titanates.

The scope of the claims should not be limited by the preferred embodiments set forth in the examples but should be given the broadest interpretation consistent with the description as a whole.

The present description refers to a number of documents, the content of which is herein incorporated by reference in their entirety.

REFERENCES

1. Rohan R. et al. *J. Phys. Chem. C* (2016), 120 (12), 6450-6458.
2. Kim Y.-S. et al. *ACS Appl. Mater. Interfaces* (2014), 6 (11), 8913-8920.
3. Pohl B. et al. *J. Electrochem. Soc.* (2015), 162 (3), A460-A464.

The invention claimed is:

1. A lithium-ion battery comprising a nitrile-based organic compound in association with an electrolyte of the battery, wherein the compound has a general formula IV outlined below

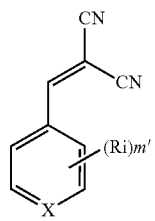

IV wherein:

X is C or N;

Ri are each independently selected from the group consisting of H, alkyl, cycloalkyl, alkene, alkyne, aryl and alkylaryl, alkoxy, thioalkoxy, OH, SH, $NH_2$, a halogen atom, a halogeno alkyl, a halogeno alkoxy, a halogeno thioalkoxy, a cyano alkyl, a cyano alkene, a cyano alkyne, CN, $NO_2$, $SO_2$, COOH and acyloxycarbonyl; and when Ri is H, m' is 5 and when Ri is not H, m' is an integer from 0 to 5.

2. The battery according to claim 1, wherein the compound has a general formula B outlined below

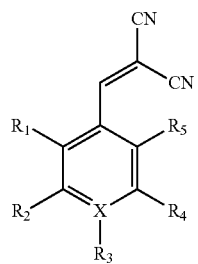

B wherein:

X is C and $R_3$ is H; or X is N; and $R_1$ to $R_5$ are each independently selected from the group consisting of H, alkyl, cycloalkyl, alkene, alkyne, aryl and alkylaryl, alkoxy, thioalkoxy, OH, SH, $NH_2$, a halogen atom, a halogeno alkyl, a halogeno alkoxy, a halogeno thioalkoxy, a cyano alkyl, a cyano alkene, a cyano alkyne, CN, $NO_2$, $SO_2$, COOH and acyloxycarbonyl.

3. The battery according to claim 1, wherein the compound is B1, B2, B3, B4, B5, B6, B7 or B8 outlined below

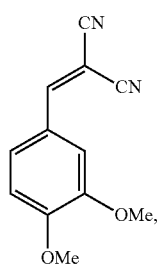

B1

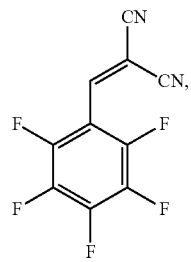

B2

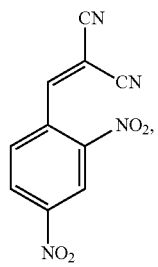

B3

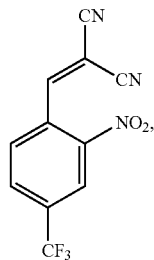

B4

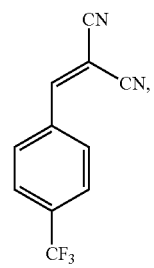

B5

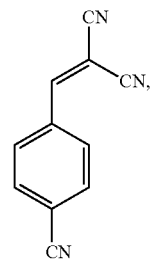

B6

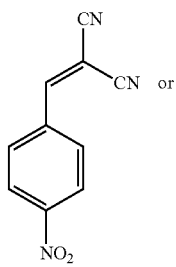

B7 or

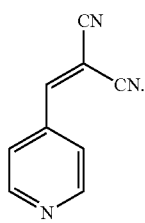
B8

4. A method of improving the performance and safety of a Li-ion battery, comprising adding a nitrile-based organic compound of claim 1 to an electrolyte of the battery.

5. The battery according to claim 1, wherein the nitrile-based organic compound is added to the electrolyte as an additive in an amount ranging from about 0.01 to about 5.0% wt.

6. The battery according to claim 1, wherein a cathode of the Li-ion battery comprises a lithium-containing material.

7. The battery according to claim 6, wherein capacity or reversibility of the battery are improved.

8. The battery according to claim 1, wherein a cathode of the Li-ion battery comprises one or more of a lithium oxide, olivine, lithium cobalt oxide (LCO), lithium manganese oxide (LMO), lithium nickel oxide (LNO), or a nickel manganese cobalt oxide (NMC).

9. An electrolyte comprising a nitrile-based organic compound of a general formula IV outlined below

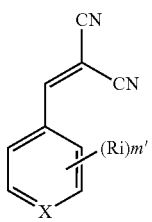
IV wherein:
X is C or N;
Ri are each independently selected from the group consisting of H, alkyl, cycloalkyl, alkene, alkyne, aryl and alkylaryl, alkoxy, thioalkoxy, OH, SH, $NH_2$, a halogen atom, a halogeno alkyl, a halogeno alkoxy, a halogeno thioalkoxy, a cyano alkyl, a cyano alkene, a cyano alkyne, CN, $NO_2$, $SO_2$, COOH and acyloxycarbonyl; and
when Ri is H, m' is 5 and when Ri is not H, m' is an integer from 0 to 5.

10. A battery comprising the electrolyte as defined in claim 9.

11. The electrolyte of claim 9, wherein the compound is B1, B2, B3, B5, B6, B7 or B8 outlined below

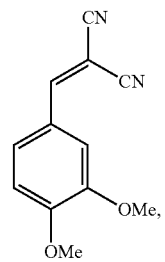
B1

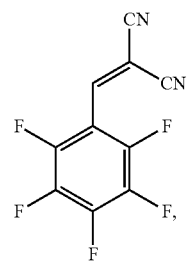
B2

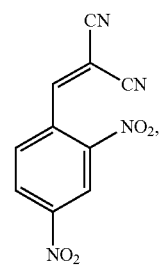
B3

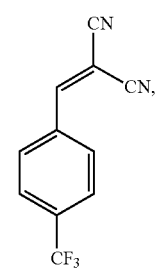
B5

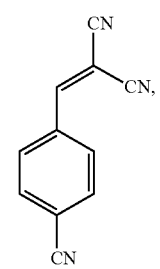
B6

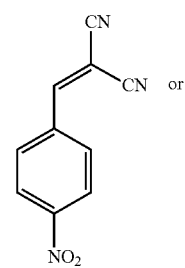
B7

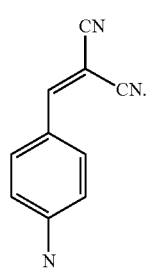
B8
* * * * *